United States Patent [19]
VonBargen

[11] Patent Number: 5,708,273
[45] Date of Patent: Jan. 13, 1998

[54] TRANSFLECTANCE PROBE HAVING ADJUSTABLE WINDOW GAP ADAPTED TO MEASURE VISCOUS SUBSTANCES FOR SPECTROMETRIC ANALYSIS AND METHOD OF USE

[75] Inventor: Kenneth P. VonBargen, Berwyn Heights, Md.

[73] Assignee: Foss NIRSystems, Inc., Silver Spring, Md.

[21] Appl. No.: 647,247

[22] Filed: May 9, 1996

[51] Int. Cl.$^6$ .................... G01N 21/25; G01N 21/01
[52] U.S. Cl. .................... 250/341.2; 250/341.8; 250/339.11; 250/339.12
[58] Field of Search .................... 250/341.2, 341.8, 250/339.07, 339.09, 339.11, 339.12

[56] References Cited

U.S. PATENT DOCUMENTS

| | | | |
|---|---|---|---|
| 4,266,878 | 5/1981 | Auer | 250/339.11 X |
| 4,540,282 | 9/1985 | Landa et al. | 356/328 |
| 5,044,755 | 9/1991 | Landa et al. | 356/440 |
| 5,278,412 | 1/1994 | DeThomas et al. | 250/341.2 X |
| 5,343,045 | 8/1994 | Gupta | 250/339.11 X |
| 5,532,487 | 7/1996 | Brearley et al. | 250/339.09 |

OTHER PUBLICATIONS

DiFoggio et al., "Near-Infrared Offers Benefits and Challenges in Gasoline Analysis", Oil & Gas Journal, May 1993, pp. 87–90.

*Primary Examiner*—Edward J. Glick
*Attorney, Agent, or Firm*—Lane, Aitken & McCann

[57] ABSTRACT

An infrared spectroscopy instrument having a transflectance type probe with an adjustable path length is disclosed. The instrument is adaptable to take both reflectivity and transmission type measurements. According to a method of use of the instrument discloses a material undergoing a change in viscosity and optical density can be measured by appropriately adjusting the path length to allow a sample of the material to enter. At a first interval, a first measurement is made using the instrument according to a transmission protocol. A second measurement is made of the sample when the sample is viscous and optically dense at a second interval using the same instrument according to a reflectivity measurement protocol.

6 Claims, 3 Drawing Sheets

TRANSFLECTANCE PROBE HAVING ADJUSTABLE WINDOW GAP ADAPTED TO MEASURE VISCOUS SUBSTANCES FOR SPECTROMETRIC ANALYSIS AND METHOD OF USE

FIELD OF INVENTION

The present invention relates to a method and apparatus used for spectrometric transmission and reflectance measurements and, in particular, NIR reflectance and transmission measurements of fluids which undergo a change in viscosity. The invention is particularly suited to the in situ analysis of pharmaceutical compositions which undergo significant physical changes during a batch manufacturing process.

BACKGROUND OF THE INVENTION

Spectrometric analysis is a non-invasive and non-destructive manner in which to determine both qualitative and quantitative properties of compositions. Infrared analysis and more particularly near-infrared ("NIR") analysis, is particularly suited to the analysis of organic compounds. The infrared absorption spectrum is highly characteristic, and is sometimes referred to as the molecular fingerprint. The natural vibrational frequencies of molecules and crystals fall within the infrared range and therefore the infrared region is valuable for the study of the structure of matter. Certain molecular bonds are prone to vibrate when exposed to characteristic wavelengths of infrared radiation which causes the molecules to absorb infrared radiation. Near infrared spectroscopy takes advantage of this activity by measuring the absorption of an unknown sample at various wavelengths throughout the near infrared range. Infrared light which is either reflected from or transmitted through a sample exhibits a highly characteristic spectrum showing the absorption of the sample at various predetermined wavelengths. The wavelength and magnitude of the absorption, as revealed in a spectrograph (a graphical representation of the absorbance values), can be used to determine information about the molecular structure and composition of the sample. Infrared spectrometry has proven to be a valuable tool for analysis of a wide variety of products including milk, grains, oils, gasoline, alcohols, and pharmaceutical products.

When measuring substances which are harmful or explosive it is often desirable to use an optical probe to interface with the sample. The probe can be directly inserted into a sample of gas or liquid which reduces the possibility of adverse exposure to the technician. In general, measuring devices used for infrared spectroscopy require a near infrared light source and a light detector contained in an instrument known as a spectrometer. Light which has been either reflected from or transmitted through a sample is broken down into narrow wavelength bands either before or after interaction with the sample. In conventional arrangements, fiber optic cables transmit the light to and from the sample in a probe which provides an appropriate interface with the sample. The narrow wavelength bands are then directed to a light detector which then transmits a signal indicative of the intensity of light. The signal is then analyzed or interpreted to yield absorbance data which in turn provides information about the constituent make-up of the sample.

Absorbance measurements are generally either reflective, transmission or transflectance. Reflectance measurements involve directing light at a sample and then collecting the light which is reflected either from the surface of a sample or from molecules or crystals contained within a sample. A portion of the light reflected from the sample is directed back to a light sensitive detector system where it is converted to a signal. In the detection operation, the output of the photodetectors is sampled at predetermined times corresponding to narrow wavelength bands to yield values which indicate the intensity of the reflected light at the bands. The analysis of reflectance measurements involves scanning a standard, often in the form of a white reflective tile. The value of the signal generated from light reflected from the standard is compared with the light reflected from the sample to yield a value representing the absorbance of the sample. Reflectance measurements are routinely employed in the measurement of solids and non-Newtonian matter such as chemical powders and solid agricultural products.

A second type of infrared analysis is referred to as transmittance or transmission which involves directing infrared light at a sample and then measuring the light which has passed through the sample. This operation requires a probe to transmit the light and an optical receiver to collect light. Incident light which has passed through the sample is collected by the receiver and is directed to a detector. The detector then generates a signal from which absorbance values of the substance being analyzed are determined. As in the case of reflectance measurements, an absorption spectrum can be created which sets forth the absorbance of the sample plotted as a function of wavelength. Transmittance measurements also require a standard or reference measurement which approximates 100 percent transmittal of radiation. Usually the reference measurement is taken with an empty sample cell or a cell containing a clear liquid. The value of the signal from light transmitted through the sample is compared with the value of the signal obtained from the standard to yield an absorbance value. Because of the limits to the instruments sensitivity, transmission absorption spectra is generally limited to samples which are relatively transparent to infrared radiation.

A third, hybrid method of spectrometric measurement is referred to as transflectance which involves the simultaneous collection of both light which has been reflected from and light transmitted through a sample. This method also involves providing an illuminating source which transmits infrared radiation to a probe immersed within the sample. Sample material can flow into a gap provided on the end of the probe which is defined by a window and an opposite mirror. Light is transmitted from the probe through the window and then through the sample where it impinges on the mirror. From the mirror light is reflected back again through the sample and back through the window where it is collected by suitable means, such as an optical fiber, and directed to a detector. In this arrangement, some of the light falls directly on matter suspended within the sample and consequently is scattered by the sample. A portion of the scattered light is directly reflected back to the collection fiber. Thus, in certain circumstances, the collection fiber captures both light which has been transmitted through the sample and reflected from the sample. Although the amount of radiation reflected from the sample is dependant on the composition of the sample, typically the reflective values from fluid samples are low. As a result, conventional transflectance instruments are designed to optimize the light which has been transmitted through the sample. Accordingly, in conventional transflectance systems the output from the detectors is measured according to a protocol designed for transmission measurements and thus the absorption values are determined by comparison to transmission standards and constants.

In the prior art it is known to provide probes having adjustable path lengths in connection with transmission measurements. One recognized advantage of an adjustable transmission probe is to narrow the path length when measuring samples which are relatively opaque to infrared light to optimize the amount of light which will pass through the sample. By providing an instrument with an adjustable path length, absorbance measurements can be kept within the optimum ranges for a given instrument. Using a probe having an adjustable path length further facilitates the technician to take a series of measurements of the sample, each at different path lengths. By comparing the results of the absorption values, errors due to problems with the instrument, such as fouling of the windows of the probe by a film, can be obviated.

Many of the prior art probes require the removal of the probe from the sampled material in order to change the path length. When dealing with materials which are highly toxic, carcinogenic, radioactive, flammable, at extremely high temperatures or pressures or undergoing a chemical reaction, it is apparent that it is desirable to be able to adjust the path length from a remote location, outside the reaction chamber. Accordingly, it is one object of the invention to provide a transflectance probe having an adjustable gap which can be adjusted to precise distances from a location outside a reaction chamber in connection with making spectroscopy measurements.

Prior art probes exhibit some difficulties when measuring samples which are viscous. For example, some manufacturing processes involve an initial stage which is characterized by a solid suspended within a liquid. During the manufacturing process, the mixture is eventually put into solution and may become transparent however in the initial phases of such a process, the mixture to be monitored may resembles a thick opaque slurry. Such mixtures are often heated and agitated to facilitate the formation of a clear solution from the suspension. In other manufacturing processes the opposite sequence occurs—a relatively transparent or translucent liquid with low viscosity becomes very viscous and virtually opaque to infrared light. Such conditions are frequently manifested in the manufacture of pharmaceutical products. It is desirable to monitor the progress of such processes in order to optimize reaction conditions or otherwise control the operating parameters. However because of the significant changes in the process and because of the presence of the some stages which involve a mixture which is opaque and very viscous, measurements are physically difficult to accomplish. In circumstances where the fluid becomes a thick slurry it is both difficult to ensure fluid will flow within the window gap provided on conventional probes and to collect sufficient light which has passed through the sample to make accurate measurements. In the past when a sample mixture was presented in such conditions the probes or infrared measurement systems would no longer be functionally employed. Despite the potential to employ information using reflectivity measurements in such circumstances, their use has been ignored or overlooked. Accordingly, it is a further object of the invention to provide a probe having an adjustable path length which will facilitate the ability of an instrument to measure fluids which exhibit a severe change in both viscosity and optical density during a process.

It is a further object of the invention to provide a single probe and spectrometer which can be alternatively used to measure a sample reaction product by either its reflectivity or its transmissivity features.

It is another object of the invention to provide a transflectance probe having an adjustable path length which has a range which enables the detector and consequent analysis to effectively disregard the effects of light which has been transmitted through a sample.

SUMMARY OF THE INVENTION

The instant invention involves an apparatus and method of infrared analysis designed for in situ monitoring of batch type reactions or processes. The apparatus according to the invention employs an infrared light source, a transflectance probe, a grating, an infrared light detector which generates a signal and a signal analyzer. Infrared light is directed from the light source to a sensing head of the probe by an optical fiber. The sensing head of the probe, designed to be completely immersed within the reactant material, has a window and mirror which can be moved with respect to each other to correspondingly adjust the path length where the sample interfaces with the light. Precise control of the path length can be performed from a location remote from the reaction chamber. The probe contains optical fibers which collect light which has been either transmitted through or reflected from the sample and directs the light to a grating where the light is divided into its constituent wavelengths bands in the NIR range. From the grating infra-red light is directed towards a detection device which generates a signal in response to the intensity of the light. Signals from the detection device are analyzed according to either reflectivity or transmissivity protocols. The respective protocols are predetermined and involve different calibrations. They are dependant on the specific reaction or process which is to be monitored and measured and the criteria governing the protocol is developed from historical data using analytical methods. The transflectance probe is designed to allow the user to adjust the path length to a maximum position where substantially no radiation is transmitted through the sample when the process is in a viscous and relatively opaque condition. Thus the probe can function in both a reflectivity mode, a transmission or a transflectance mode.

According to a preferred method of use of the device, when the sample initially has a low viscosity and is at least relatively transmissive or transparent, an initial series of measurements is made with the gap set to a narrow dimension to facilitate transmission measurements of the sample material. As the material undergoing the reaction becomes more viscous, the gap of the probe may be increased in width to facilitate flow of the more viscous material through the gap. In the later stage of the process the probe is designed to measure, the reactant product becomes very viscous and more opaque to infrared light. In such circumstances transmission measurements can not be made effectively because the intensity of light which is transmitted through the sample material is diminished to such a degree that it is difficult to obtain sufficient data from light which passes through to obtain reliable measurements. According to the method of the invention, measurement of the sample material is continued under these conditions by positioning the probe at its maximum path length distance so that essentially no transmission through the sample occurs and the reflectance of the sample is measured. In this mode the analysis of the signal is interpreted according to a reflectivity protocol. Because the probe is adjustable, the same probe used in connection with the transmission measurements can be employed as the sample material radically changes its chemical and physical characteristics. In a preferred embodiment, when the reflectivity measurement is performed the path length is set at a maximum length, in order to prevent transmission of the infrared light though the sample and thus prevent interference with the reflectivity measurement. Because of the relatively long distance of the path length, the amount of light which is transmitted through the sample is de minimis.

In accordance with another method of the invention, the material which is to be measured is initially in an opaque and viscous state. For example, a solid in powdered or crystallized form is introduced to a liquid to result in a thick slurry. Accordingly, in the initial stages of the process, measurements are made with the path length at its maximum width and a reflectivity protocol is followed. The mixture is then heated and stirred until it transforms to a transparent or translucent condition. As the mixture is heated, it also becomes less viscous and can flow into the gap of the probe without difficulty. Measurements are made by the instrument according to the transmission protocol at these later stages of the process.

BRIEF DESCRIPTION OF THE DRAWINGS:

FIG. 8b is a top view in elevation of the pin shown in FIG. 8a.

DETAILED DESCRIPTION OF THE PREFERRED EMBODIMENTS

Figure 1:
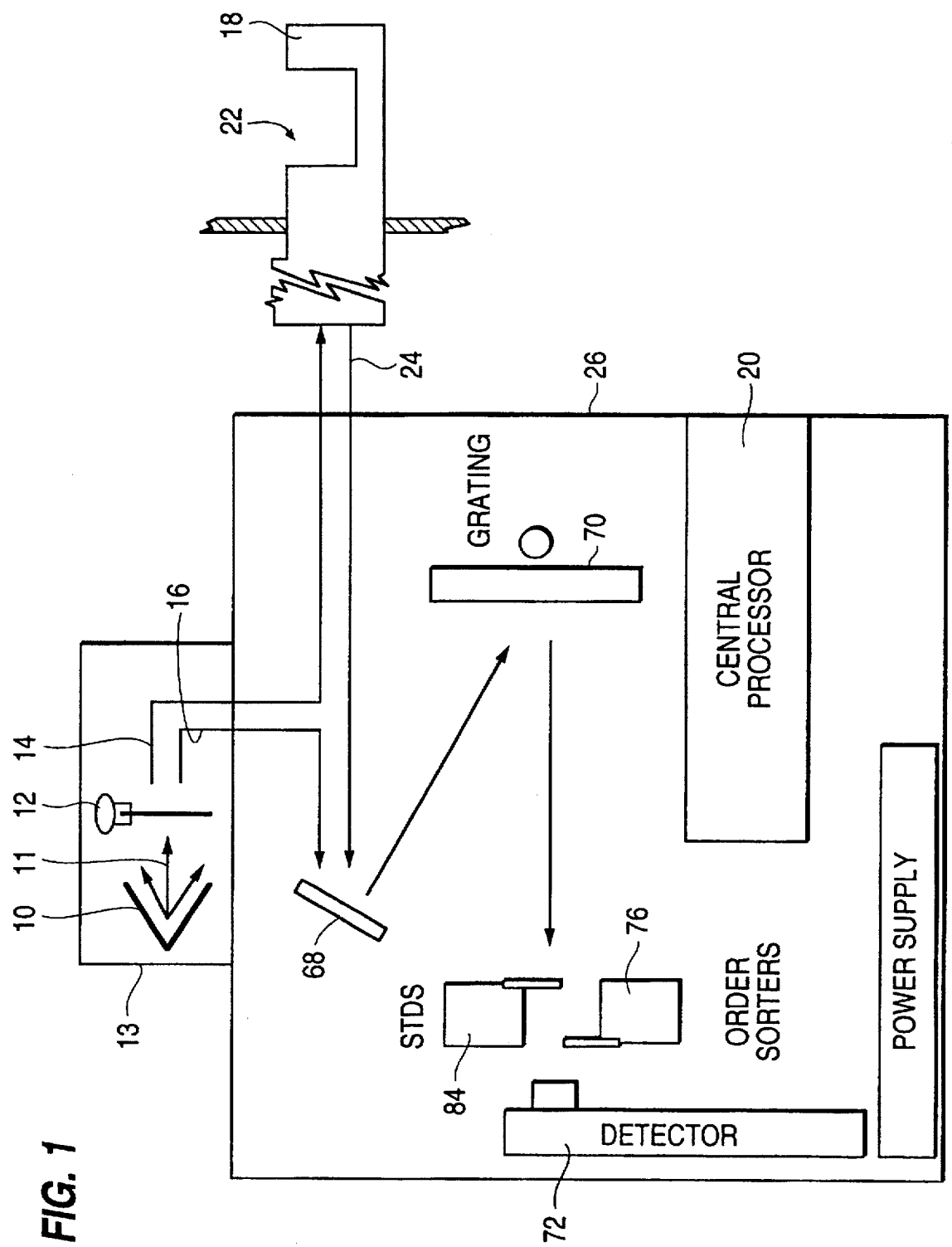
FIG. 1 is a schematic plan view of the optical measuring system according to the invention.

Referring now to FIG. 1, the apparatus according to the invention has a near-infrared ("NIR") light source 10 which sends a continuous beam 11 of infrared radiation past a shutter 12 where it can impinge on either the end of optical fiber bundles 14 or bundle 16. The light source 10, shutter and the respective fiber optic bundle ends are contained by an enclosure 13. Operation of the shutter controls the NIR light to impinge on either illuminating fiber bundle 14 or reference bundle 16. The shutter can be closed to prevent all NIR light from entering the instrument. The shutter is operated in response to a command from the central processing unit 20 located within an optical enclosure 26.

The fiber optic bundle 14 provides a link or conduit to transmit infrared light from the NIR source 10 to a probe generally designated by reference numeral 18. The probe 18 provides an interface with the sample material 22 which is to be analyzed. A third bundle of collection optical fiber 24 originates in probe 18 and terminates adjacent to fiber optic bundle 16 inside the optical enclosure 26 of the instrument. The second fiber optic bundle 16 serves as a reference fiber and guides light from the source directly to the optical enclosure. The arrangement can thus be characterized as a split beam which provides infrared light at a relevant value which can be compared against the light which interacts with the sample. Accordingly any fluctuations in the intensity of the light source can be appropriately accounted for in the analysis operation. The reference fiber also eliminates the need for a standard in the reflective mode because the fiber can serve as a surrogate for a reflective standard.

Figure 2:
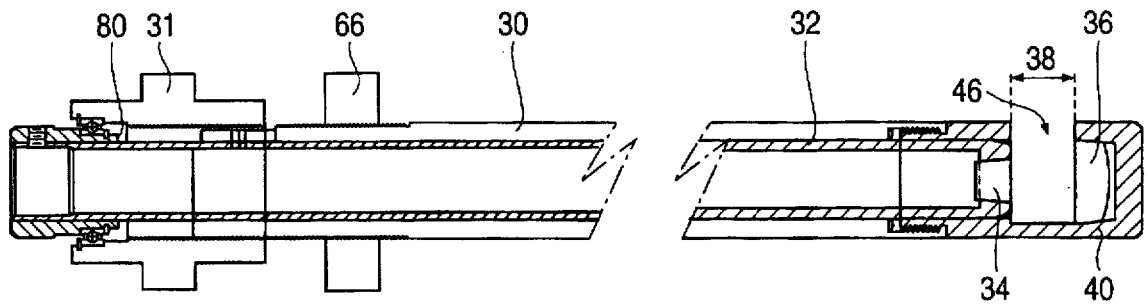
FIG. 2 is a side sectional view of the probe assembly according to the invention.

Now referring to FIG. 2, probe 18 consists of an outer cylindrical housing 30 having a smooth interior bore which receives an inner tubular element 32. Inner tubular element 32 surrounds a fiber optic bundle which contains both the illuminating fibers 14 and the collecting fibers 24 all of which terminate at a window 34. Window 34 is comprised of sapphire or other suitable material which is both impervious to the sample material and can otherwise withstand the environment of the reaction chamber. Sapphire is characterized by good chemical inertness and excellent transmission properties, particularly for near-infrared wavelengths and is the preferred material for the window. In axial alignment with window 34 is mirror 36. Mirror 36 is also formed of sapphire and has a surface coated with an appropriate reflective material such as gold to reflect infrared light back to the collecting fibers. Window 34 and mirror 36 define the sample area 38 which, as discussed in more detail below, can be adjusted by sliding the inner tubular element 32 towards the mirror. The sample area is the location into which a sample material can flow and can be subjected to infrared light. Mirror 36 is held in a fixed position with respect to the outer housing 30 and is positioned on a removable tip 40 of the probe 18.

Figure 3:
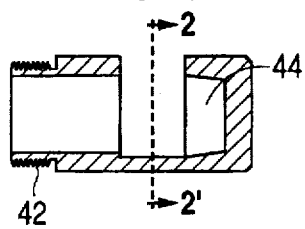
FIG. 3 is a side sectional view of the probe tip.
Figure 4:
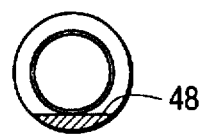
FIG. 4 is an sectional view of the tip of the probe taken along line 2—2 showing the cavity which receives a reflective surface.

As best seen in FIG. 3, tip 40 has threads 42 on the exterior surface designed to engage opposite treads on housing 30. An annular cavity 44 is slightly chamfered and designed to precisely receive mirror 36. Transversely, intersecting tip 40 is slot 46 which effectively defines the maximum area through which the sample can flow. The axial dimension of the slot is approximately 0.4 inches. FIG. 4, an axial view of the tip, shows that the bottom of the slot is defined by a flat surface 48 and the slot generally has a rectangular profile which allows fluid to freely pass into the sample area in a direction perpendicular to the axis of the probe.

Figure 5:
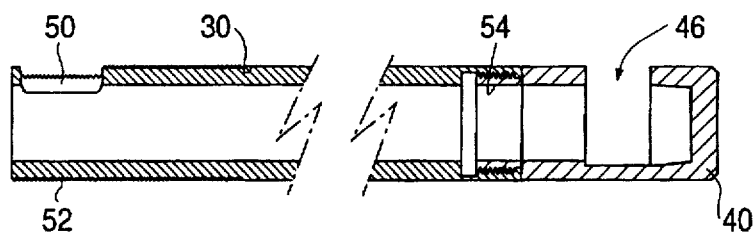
FIG. 5 is another side sectional view of the outer casing showing the casing in engagement with the tip of the probe.

Now referring to FIG. 5, a bottom view of the housing, shows an ovular opening 50 on the top of the cylindrical sidewall. FIG. 5 further shows the housing 30 in engagement with the tip 40. Threads 54 are provided on the interior surface of one end of the cylindrical housing 30 which engage threads 42 of the tip. On the end opposite the tip, threads 52 are provided on the outside surface of the housing 30 which engage a casing 60 as further shown in FIG. 6.

Figure 6:
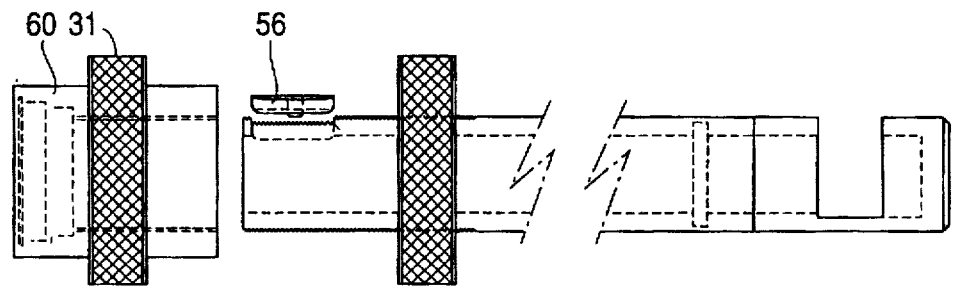
FIG. 6 is a side view in elevation of the retainer assembly, the pin, the outer casing and tip of the probe.
Figure 7:
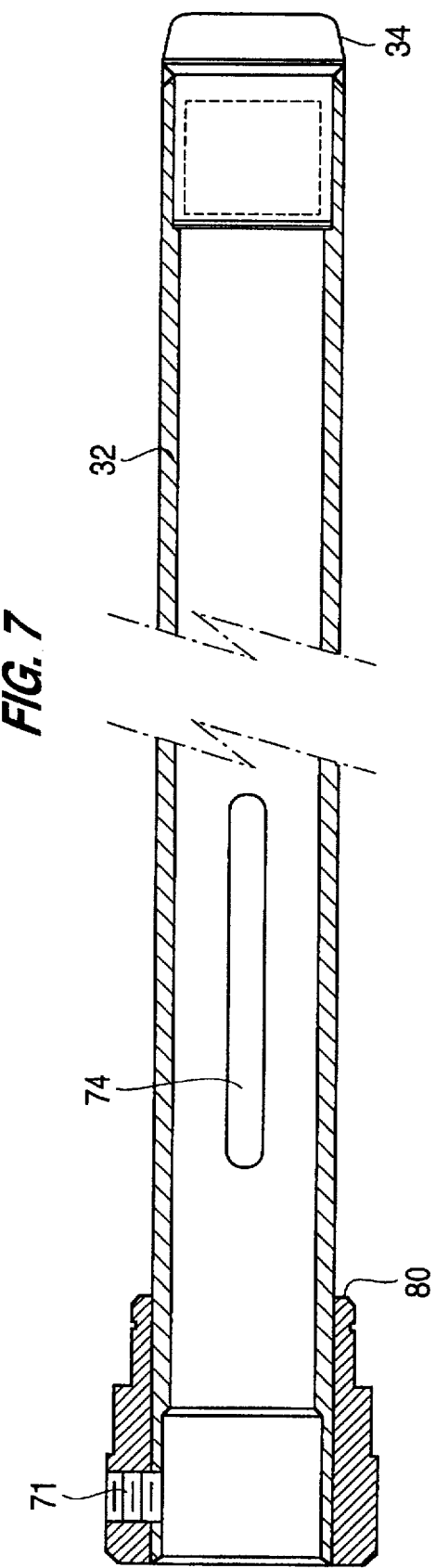
FIG. 7 is a bottom sectional view of the tubular inner element and window assembly of the probe.
Figure 8C:
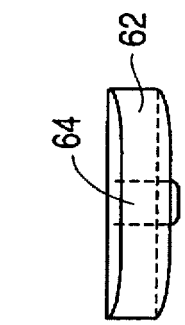
FIG. 8c is a side view in elevation of the pin shown in FIGS. 8a and 8b.
Figure 8B:
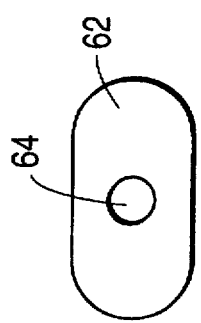
Figure 8A:
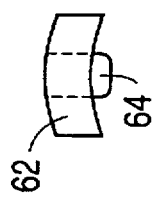
FIG. 8a is a front view in elevation of the pin which engages the barrel of the probe.

FIG. 6 shows a pin 56 which serves to limit the axial movement of the tubular element 32 within the housing 30 and prevent rotational movement of the tubular element 32 with respect to the housing. The pin is received within ovular opening 50 and is formed so that it does not protrude beyond the exterior surface of housing 30 and thus housing can be received unimpeded within casing 60. The pin remains in a fixed position. FIGS. 8a–c further show the construction of the pin which is formed by a head 62 which has an arcuate profile which mirrors the curve formed by the cylindrical walls of the outer housing. A shank 64 extends perpendicular to the axis defined by the housing and protrudes into the tubular passage section defined by the housing 30. Now referring to FIGS. 8a–8c, the shank 64 of the pin is designed to be received in the elongate slot 74 provided on the top surface of the inner tubular element 32. The slot 74 is illustrated in FIG. 7. The engagement of the pin within the slot 74 prevents the inner tubular element 32 from rotating within the housing 30 and limits the axial movement of inner tubular member with respect to the housing. Window 34, which provides for the interface between the infrared light and the sample is secured to the end of the tubular element 32 and thereby caps and seals the inner tubular element which contains the optical fibers. On the opposite end of the inner tubular element 32 a threaded passage 71 is formed perpendicular to the axis which can receive a bolt. The bolt secures the fiber optic bundles (not shown) which lead to and from the window 34.

Now referring back to FIG. 1 both the reference fiber 16 and the collecting fiber 24 are directed to mirror 68 which directs both the infrared light which has interfaced with the sample and the light which has been collected directly from the source to a grating 70. The grating disperses the infrared radiation into a spectrum and directs specific wavelengths of light to the detector 72 in response to the oscillation of the grating. According to the preferred embodiment of the invention as depicted in FIG. 1, a post-dispersive grating monochrometer is employed. However, it is contemplated that other manners of dispersal would also be effective. For example, the infrared radiation could be divided into bands before interacting with the sample. Adjacent to the light path between grating 70 and detector 72 are standards 84 which can be periodically positioned into the light path when the instrument is instructed by the central processing unit to perform measurements using a protocol for transmission measurements. The standards may be positioned in the path of light in response to a command from a central processing unit 20 at predetermined times. Before reaching the detector the light may also be filtered through an appropriate order sorter 76 so that higher order wavelengths are removed. The order sorter filters 76 are also controlled by central processing unit 20 to coordinate the interposition of the correct filter for the wavelength which is passing from the grating to the detector.

As the grating oscillates, light for each wavelength impinges on detector 72 a signal is created which reflects the intensity of the light. The electric signal generated by the photodetector is transmitted to an analyzer which translates the signal into useful information regarding the absorbance properties of the sample. Application of an algorithm to the signal interprets quantitative and qualitative aspects of the sample. It is contemplated that other types of analysis could be employed including artificial intelligence techniques or intuitive analysis by experts who can analyze graphical representations of the data by comparing the unknown data with the graphs of known compounds.

In order to operate the instrument, it first must be calibrated and the constants of appropriate algorithms must be determined. This operation involves making measurements of the process with the instrument at a series of intervals while simultaneously physically removing a sample of the material undergoing the process. The sample is then analyzed by traditional analytical chemistry methods—e.g. Gas chromatography, titration, or use of specific reagents. The results of the analytical tests are then correlated to the infrared scans taken at the time of the sample and a mathematical model is created. This procedure is referred to as the reference step which is repeated a number of iterations throughout several processes in order to obtain accurate data for a number of reference runs. During the reference runs the path length of the probe is set at different distances which is also recorded and each spectrum is correlated with the results from the analytical testing to provide values for the respective spectrums. For each given manufacturing process, a data base or a calibration sample set is created. Then a mathematical process is employed, such as a multivariant regression analysis or multilineal regression, to correlate the signature of the unknown spectrum to the known values and determine constants for algorithm to analysis material being processed. The instrument thus provides an output which may reflect both qualitative and quantitative information regarding the material.

The measurement with the instrument according to the invention involves immersing the tip or sensing head of the probe into the sample which is undergoing either a chemical or physical change. If the process is one in which the early stages of the process is a fluid in the nature of an opaque suspension which is going into solution, the operator initially operates the probe in a reflectance mode. Thus, referring to FIG. 2, the adjustment disk 31 is rotated to position mirror 36 at its maximum distance away from the window 34. This distance is measured by an electronic gauge and the value is provided as input to the central processing unit when a command is provided to scan the sample. At the maximum path length, the sample material can readily flow into the gap and essentially no transmission through the sample occurs. In response to the command to scan the sample, the shutter is opened and a full spectrum of near-infrared light is directed in sequence through the fibers 14. At alternating time intervals, the full infrared spectrum is also directed through the reference fiber 16. In order to ensure that fluctuations in the intensity of the light source do not adversely effect the measurement, the absorption or reflectivity values is determined by comparing the values of the signal generated from collection fiber from the value determined from the reference fiber. The use of the reference fiber eliminates the need for measurements from both a reflective tiles as is customarily practiced in conventional reflectivity measurement and from an empty sample chamber cell as used in conventional transmissivity measurements.

During the initial phases of the measurement as described above the constants used in the algorithm which determine the quantitative and qualitative data selected from those previously stored for the measurement at the same time and gap distance. When the reaction has progressed to a point that the reactant mixture becomes relatively transparent, transmission measurements are carried out by rotation of adjustment ring 31 to narrow the path length. The width of the path is narrowed to the degree permitted by the viscosity to enable an effluent transmission to be made. Rotation of the adjustment ring engages the threads 52 on the outer surface of the housing and draws the housing towards the casing 60 and towards seat 80 found on a flange section of the inner tubular member 32. As the housing 30 is moved towards the seat the mirror 36 approaches window 34. As the mirror approaches the window, the path length is decreased. The mirror and window can be adjusted to precise distances with respect to one another which are detected by the gauge.

In connection with processes characterized by initial stages which are transparent or translucent, the instrument is initially operated according to conventional transmission procedures. As the reaction progresses, the sample material becomes thick and virtually opaque to NIR light. At this juncture, measurement of the process can proceed by opening the gap of the pore to its maximum width and employing a reflectivity measurement protocol.

The advantages of the invention which integrates past measurement methodologies are immediately apparent. While the measurements of analogous processes in the past may have required the use of multiple probes, the present invention employs a single probe which is used throughout a complete transformation of a material. A separate reflectivity probe, with its concomitant standards and instrument which in the past may have been used when the reactant mixture is unsuitable for transmission measurements is no longer necessary. Using a single probe and instrument has the obvious advantage of decreasing the costs associated with installation of the instrument on the reaction vessel and the costs of the instruments themselves.

The invention described above is of preferred embodiments of the invention and modification may be made thereto without departing from the spirit and scope of the invention.

I claim:

1. A method for periodically monitoring a material undergoing a change in viscosity and optical density using a near infrared spectrometer, said spectrometer further comprising a transflectance probe which has a sample area with an adjustable path length and an analyzer, said method comprising:

immersing said probe within said material;

setting the sample area of the probe to have a first path length, conducting a first scan of said material with said sample area at said first path length;

providing an input value to said analyzer corresponding to the first scan, analyzing said input value of said first scan according to a predetermined first protocol, changing the sample area of said probe to a second path length different than said first path length, conducting a second scan of said material with said sample area at said second path length, providing an input value to said analyzer corresponding to said second scan, analyzing said input value of said second scan according to a second protocol, wherein one of said first and second scans involves taking a measurement with the probe set at a path length set at its maximum degree and the corresponding protocol employed in said analyzer for said one of said scans uses an algorithm programmed with constants determined from reflectivity measurements.

2. A method of taking a measurement of an initially opaque material in a vessel undergoing a chemical reaction with a transflectance probe, said transflectance probe having an adjustable gap, comprising the steps of first opening said gap to a maximum width thereby allowing the material to flow within the gap, exposing the material to infrared radiation, detecting radiation with a detector which is reflected by the sample, said detector generating a signal, analyzing said signal according to a reflectivity protocol, said protocol employing a predetermined algorithm and constants, said constants determined by the analytical analysis of previous analogous materials undergoing an analogous measurement condition, then adjusting said gap to a narrower width as the material in said gap becomes more transparent, and then exposing said material to infrared radiation to make transmission measurements on the material in the gap while said gap is at said narrower width.

3. An infrared spectrometer for measuring a sample comprising, an infrared radiation source, said radiation source positioned adjacent to the ends of a first fiber optic bundle and a second fiber optic bundle, said first optic bundle serving to transmit light from said radiation source to a sample interface area, said sample interface area provided in a transflectance probe, said second fiber optic bundle serving as a reference fiber, a third fiber optic bundle originating adjacent to said sample interface area in said probe, said third fiber optic bundle serving to collect radiation either reflected from or transmitted through said sample, said second and third fiber optic bundles terminating adjacent to one another and capable of directing radiation to a detector, wherein in response to exposure to infrared radiation, said detector provides signals, means to transmit said signals to an analyzer means which, according to predetermined instructions, analyzes said signals according to either a transmission or reflectance protocol;

said transflectance probe further comprising an inner barrel and an outer sleeve, said inner barrel having a window capping one end and said first and said third bundles terminating at said window, said outer sleeve provided with a tip, said tip receiving a reflective surface positioned opposite said window and thereby forming a sample area, said probe further having means to move said outer sleeve with respect to said barrel and thereby adjust a path length of said sample area.

4. The apparatus as recited in claim 3, wherein said means to move said sleeve is provided at a location remote from said sample area.

5. An infrared spectrometer comprising:

an infrared radiation source, illuminating optical fibers, collecting optical fibers, a housing defining a tubular passageway containing said optical fibers;

a sample area having an adjustable size, means to move said illuminating and collection fibers axially within said tubular passageway relative to said housing to adjust the size of said sample area, said collecting fiber optics transmitting infrared radiation from said sample area to a photodetector, wherein in response to infrared radiation said photodetector provides a signal, said signal is transmitted to an analyzer which, according to a predetermined instruction, analyzes said signal according to either a transmission or reflectance protocol.

6. A method of taking infrared spectroscopy measurements for qualitative and quantitative analysis using a spectroscopy instrument having a probe having an adjustable path length comprising a first step of calibrating said spectroscopy instrument to a specific process, said calibration step comprising the steps of scanning a sample with infrared light throughout the infrared spectrum, detecting light either reflected or transmitted through the sample with a detector and determining an absorption value for each band length within said spectrum, a step of physically sampling the material when the sample is scanned and performing quantitative and qualitative analytical analysis on the sample to determine the constituent makeup when the sample is being scanned, repeating said steps of said calibration step a plurality of iterations at different predetermined times and different path lengths during said process to yield a data set which is characteristic of the process and the conditions of the measurements, a further step of determining an algorithm which relates the constituent makeup determined by said analytical analysis to the absorption values determined by said instrument, storing said algorithm in a central processing unit, and a measurement step comprising taking a scan of a sample having unknown characteristics, providing as input to the central processing unit the operating conditions of the measurement, and application of the algorithm to the absorption values to yield qualitative and quantitative information regarding the sample.

* * * * *